United States Patent
Lawhorn et al.

(10) Patent No.: US 7,467,871 B2
(45) Date of Patent: Dec. 23, 2008

(54) OPHTHALMOLOGICAL INSTRUMENT STAND

(75) Inventors: Steven Lee Lawhorn, Maineville, OH (US); Neil Fralick Smith, Hanover, PA (US)

(73) Assignee: Reliance Medical Products, Inc., Mason, OH (US)

( * ) Notice: Subject to any disclaimer, the term of this patent is extended or adjusted under 35 U.S.C. 154(b) by 460 days.

(21) Appl. No.: 10/978,550

(22) Filed: Nov. 1, 2004

(65) Prior Publication Data

US 2005/0092874 A1    May 5, 2005

Related U.S. Application Data

(60) Provisional application No. 60/516,549, filed on Oct. 31, 2003.

(51) Int. Cl.
*A61B 3/00* (2006.01)
(52) U.S. Cl. .................. 351/245; 351/244; 351/246
(58) Field of Classification Search .............. 351/245, 351/246, 244
See application file for complete search history.

(56) References Cited

U.S. PATENT DOCUMENTS

| | | | | |
|---|---|---|---|---|
| 3,872,593 A * | 3/1975 | Thornton et al. | ............... | 433/28 |
| 4,643,547 A * | 2/1987 | Collins et al. | ............... | 351/245 |
| 5,696,574 A | 12/1997 | Schwaegerle | ............... | 351/245 |
| 5,717,480 A * | 2/1998 | Brooks et al. | ............... | 351/221 |
| 5,907,387 A | 5/1999 | Schwaegerle | ............... | 351/200 |
| 6,022,088 A * | 2/2000 | Metzler | ............... | 312/209 |
| 6,095,649 A | 8/2000 | Brooks et al. | ............... | 351/221 |
| 6,264,329 B1 | 7/2001 | Brooks et al. | ............... | 351/221 |
| 6,335,861 B1 * | 1/2002 | Ramsey et al. | ............... | 361/686 |
| 6,575,575 B2 * | 6/2003 | O'Brien et al. | ............... | 351/245 |

* cited by examiner

*Primary Examiner*—Scott J Sugarman
*Assistant Examiner*—Brandi N Thomas
(74) *Attorney, Agent, or Firm*—Wood, Herron & Evans LLP

(57) ABSTRACT

An instrument stand for supporting ophthalmological instruments. The instrument stand may include a console housing configured to receive differently-configured electronics modules. In addition to, or instead of, the interchangeable electronics modules, the console housing may also be provided with a removable shelf that is resistant to unintentional removal during use. In addition to, or instead of, the interchangeable electronics modules and removable shelf, the instrument stand may also include a support arm having a cutout on different surfaces so that a panel carrying electrical inserts may be positioned in the cutout on one of the surfaces, while covering the unused cutout on the other surface with a blank panel.

17 Claims, 7 Drawing Sheets

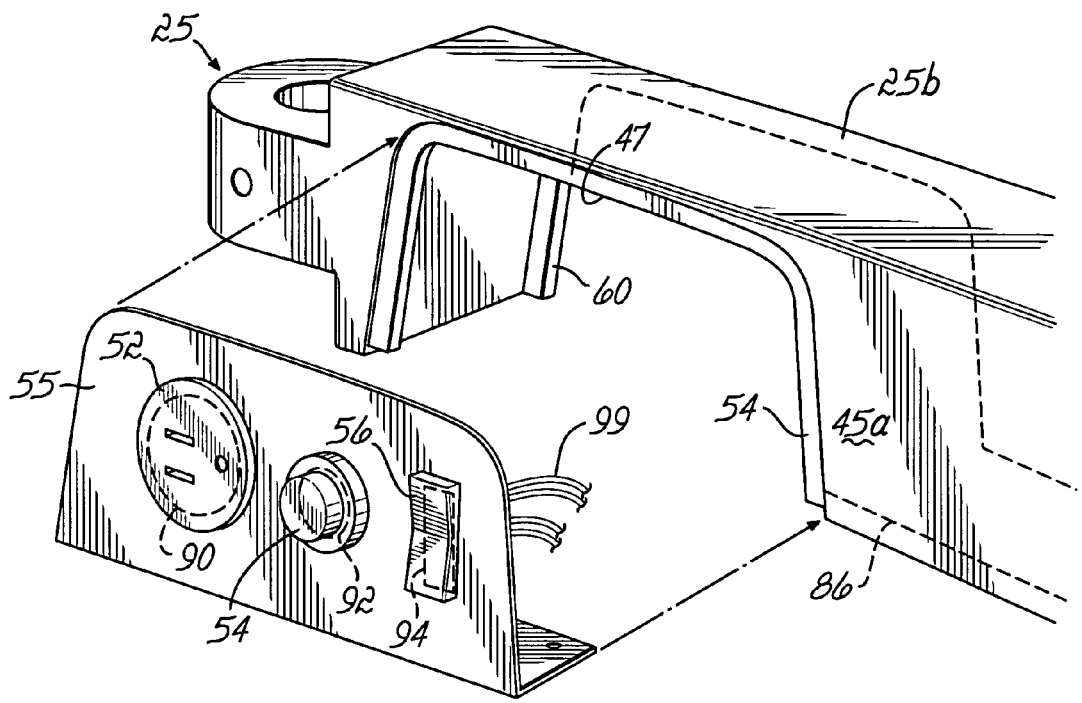
FIG. 6A
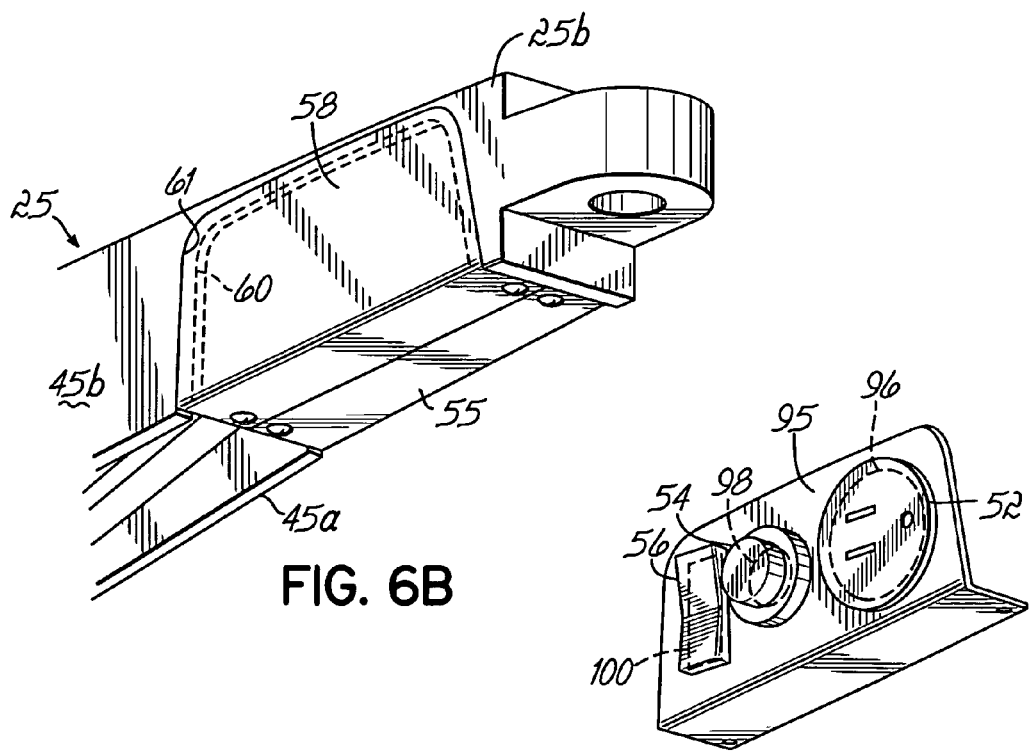
FIG. 6B
FIG. 6C

OPHTHALMOLOGICAL INSTRUMENT STAND

CROSS-REFERENCE TO RELATED APPLICATIONS

This application claims the benefit of U.S. Provisional Application No. 60/516,549, filed Oct. 31, 2003, the disclosure of which is hereby incorporated by reference herein in its entirety.

FIELD OF THE INVENTION

This invention generally pertains to instrument support mechanisms and, more particularly, to ophthalmological instrument stands.

BACKGROUND OF THE INVENTION

The medical industry relies on various types of instrument support mechanisms for supporting medical instruments proximate a seated patient. For example, ophthalmic instruments, such as slit lamps, indirect ophthalmometer, and a vision tester, must be supported in line with a patient's field of vision during eye examination procedures while the patient is seated in an examination chair. These instruments are typically placed on one or more movable instrument support arms extending from a support pole forming part of an instrument stand. The instrument stand further includes a base that supports and stabilizes the support pole. Typically, electronics in the base controls the various ophthalmic instruments and other electrical devices in the examination room, such as the room lights.

One difficulty with conventional instrument support mechanisms is the inability to easily repair the electronics and electrical circuitry found in the base of the instrument stand because a technician must disassemble the entire base to provide access. A related difficulty with conventional instrument support mechanisms is the inability to easily replace the electronics and electrical circuitry in the base of the instrument stand. For example, the stand electronics and electrical circuitry cannot be easily modified to add or remove support for instrument wells.

Some conventional instrument support mechanisms include articulated support arms featuring an electric panel carrying various electrical inserts, like switches and power outlets. Another difficulty with conventional instrument support mechanisms is that the electric panel cannot be moved to, for example, customize the instrument support mechanism for use by either a left-handed or a right-handed practitioner. Instead, the entire support arm must be replaced to adapt to the practitioner, which is costly and inconvenient.

Other conventional instrument support mechanisms include a shelf on top of the base. To be able to thoroughly clean the shelf, it should be removable from the base. However, such removable shelves may be inadvertently dislodged from the base by a horizontal force and either fall to the floor or need to be returned to the original position.

What is needed, therefore, is an instrument stand that addresses these and other deficiencies of conventional instrument stands.

SUMMARY OF INVENTION

In one embodiment of the present invention, an instrument stand includes a base having a console housing with a module-receiving space and a plurality of electronics modules each configured to be coupled with the module-receiving space of the console housing. The electronics modules are interchangeably received in the module-receiving space so that the instrument stand can be reconfigured for different applications by changing the electrical circuitry and electrical components.

In another embodiment of the present invention, an instrument stand includes a console housing having a support surface defining a horizontal plane and a side wall surrounding the support surface. The instrument stand further comprises a shelf removably supported on the support surface. The shelf has side edges and a front edge connecting the side edges. The side edges are shaped to match the side wall so that the shelf cannot be removed from the console housing by a force applied to the shelf in the horizontal plane.

In another embodiment of the present invention, an instrument stand includes a base and a support arm extending from the base. The support arm includes an interior space and first and second surfaces each including at least one cutout providing access to the interior space. The instrument stand further includes a first panel removably mounted to the first surface and a second panel removably mounted to the second surface. The first panel covers the at least one cutout in the first surface to block access to the interior space. The second panel includes at least one electrical insert positioned in the at least one cutout in the second surface.

In another aspect of the present invention, an instrument stand comprises a base having a removable back cover and an opening defined in the back cover. The stand further includes a plurality of receptacles each configured to be installed in the opening after the back cover is removed from the base. Each of the receptacles is capable of being powered by the instrument stand for energizing a device having a power cord plugged into the corresponding receptacle. The receptacles are interchangeably received in the opening so that the installed receptacle can be changed to conform to different types of plugs on the device power cord.

In another aspect of the present invention, an instrument stand comprises a base, a support arm extending from the base, and a counterweight positioned inside the base. The support arm is adapted to telescope relative to the base. The counterweight is adapted to move responsive to telescoping movement of the support arm relative to the base. The instrument further includes a cable coupling the support arm with the counterweight and a pulley mounted inside the base. The pulley has a portion in contact with the cable and the cable causes rotation of the pulley when the counterweight moves. A curved restraining member extends across at least the portion of the pulley in contact with the cable. The curved restraining member prevents the cable from becoming disengaged from the pulley under certain circumstances.

In another aspect of the present invention, a method of configuring an ophthalmological instrument stand includes removing a first electronics module from a module-receiving space defined in a console housing of the instrument stand and installing a second electronics module in the module-receiving space vacated by the removed first electronics module. The first and second electronics modules are each configured with circuitry for controlling a device associated with the ophthalmological stand.

Various additional advantages and features of the invention will become more readily apparent to those of ordinary skill in the art upon review of the following detailed description taken in conjunction with the accompanying drawings.

BRIEF DESCRIPTION OF DRAWINGS

FIG. 6A is a disassembled perspective view of a portion of the support arm of FIG. 1 showing a cutout on one side of the support arm and a panel with electrical inserts that is positioned in the cutout;

FIG. 6B is a perspective view similar to FIG. 6A taken on an opposite side of the support arm in which the cutout is covered by a blank panel;

FIG. 6C is a perspective view of a panel optionally positioned in the cutout of FIG. 6B, after the blank panel is removed and positioned over the cutout on the opposite side of the support arm, to change the location of the electrical inserts on the support arm.

DETAILED DESCRIPTION

References herein to terms such as "vertical," "horizontal," etc. are made by way of example, and not by way of limitation, to establish a frame of reference. It is understood various other frames of reference may be employed without departing from the spirit and scope of the invention.

Figure 1:
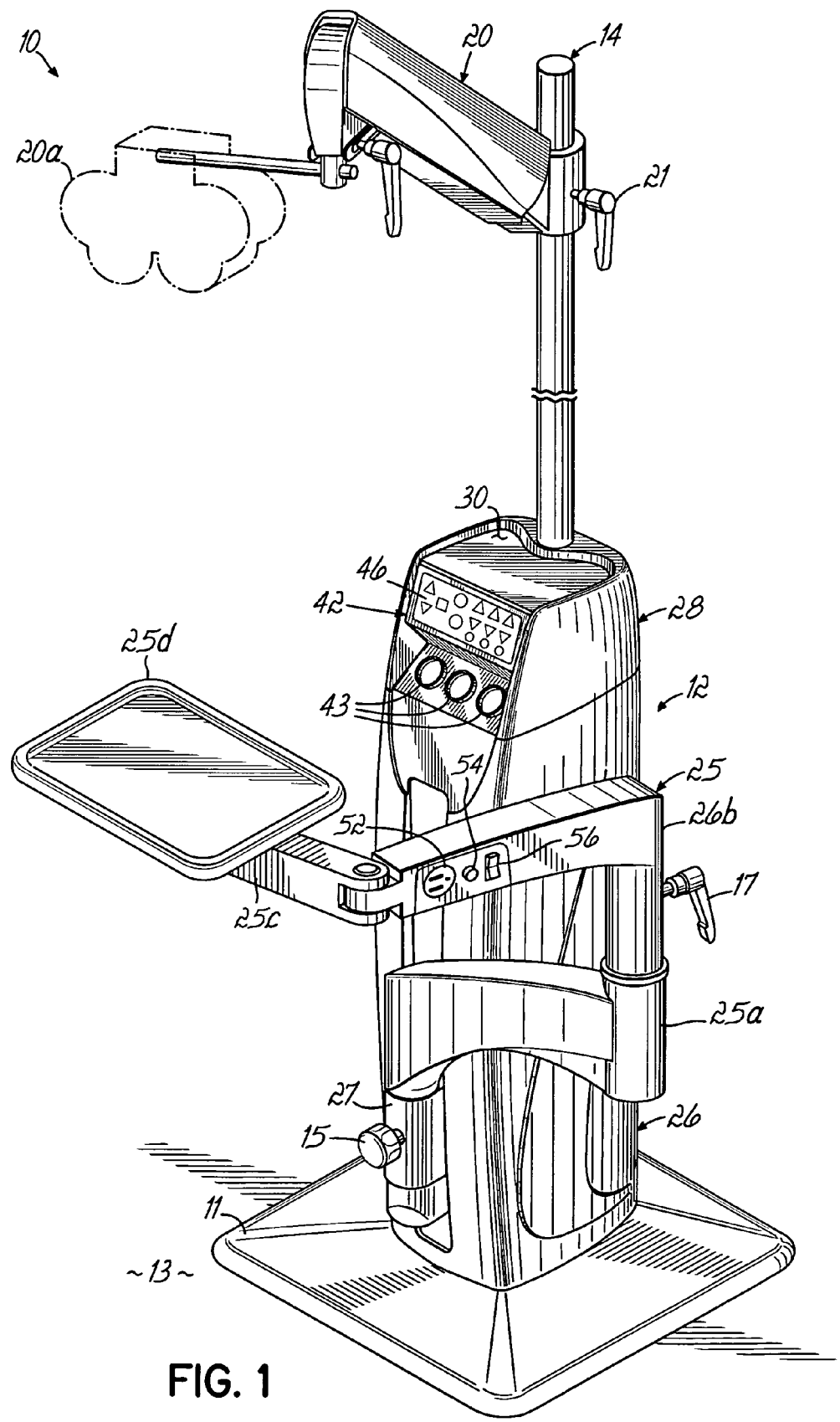
FIG. 1 is a perspective view of an instrument stand in accordance with the present invention.
Figure 2:
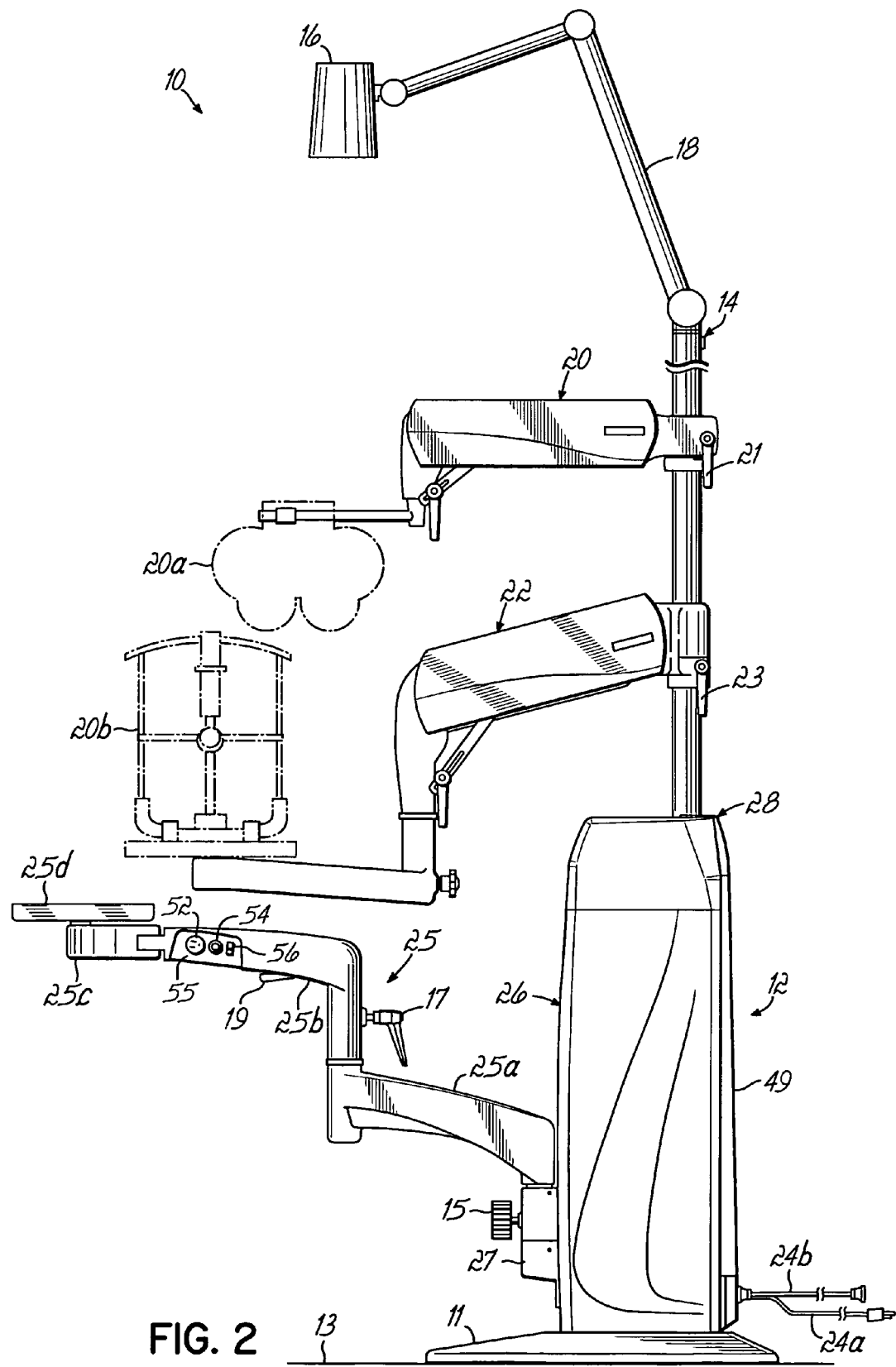
FIG. 2 is side view of the instrument stand of FIG. 1 in which an overhead lamp assembly and an additional arm assembly are mounted on the pole.

With reference to FIGS. 1 and 2, an ophthalmological support mechanism or instrument stand 10 includes a base 12 having an enlarged portion 11 supported on a room floor 13 and a tubular column or support pole 14 extending vertically from the base 12 upward toward the room ceiling. The ophthalmological instrument stand 0.10 includes an overhead lamp assembly consisting of an overhead lamp 16 and an adjustable boom 18 attaching the overhead lamp 16 to support pole 14. The boom 18 is jointed so that the overhead lamp 16 may be repositioned for aiming the light emanating from the lamp 16.

Attached to the support pole 14 are additional support arms 20, 22 each used to suspend a corresponding medical instrument 20a, 20b at a position extended laterally from the support pole 14. Medical instrument 20a, 20b may be any conventional ophthalmological instrument, such as a vision tester, a keratometer, a slit lamp with a chin rest, or any ophthalmic or optical instrument. Additional arms or support structure may be connected to the support arms 20, 22.

Each of the support arms 20, 22 is adjustable in height relative to the base 12 along the vertical extent of support pole 14 and rotatable about the support pole 14, typically in a horizontal plane. Following a position adjustment, each of the support arms 20, 22 is locked in position by a corresponding one of locking mechanisms 21, 23 actuated by, for example, a locking lever or locking knob. As such, the support arms 20, 22 are individually movable for placing the respective supported ophthalmic instruments 20a, 20b into an operative position directly in front of a patient seated in an examination chair (not shown) proximate to the ophthalmological instrument stand 10.

Base 12 includes an upwardly-extending lower housing 26 with a flared bottom, which is designed to create stable support with the floor 13, and a console housing 28 situated at the apex of the lower housing 26. Routed into the lower housing 26 is a cable 24a that provides electrical service for powering the medical instruments 20a, 20b. A chair control cable 24b for a remote switch is also routed into the lower housing 26.

Extending outwardly from a mount 27 on the base 12 is an articulated support arm 25 that includes relatively-movable sections 25a-c and a support surface 25d supported by section 25c. Section 25a is pivotally mounted within mount 27, section 25b is pivotally coupled with section 25a and may also telescope relative to section 25a for changing the height of the support surface 25d, and section 25c is pivotally coupled with section 25b. Locking mechanisms 15, 17 are used to fix the relative positions of the sections 25a-c. The ability of sections 25a-c to relatively pivot is beneficial for adjusting the lateral location of support surface 25d, which may be used to support another medical instrument (not shown), in front of a seated patient.

Figures 3, 3A:
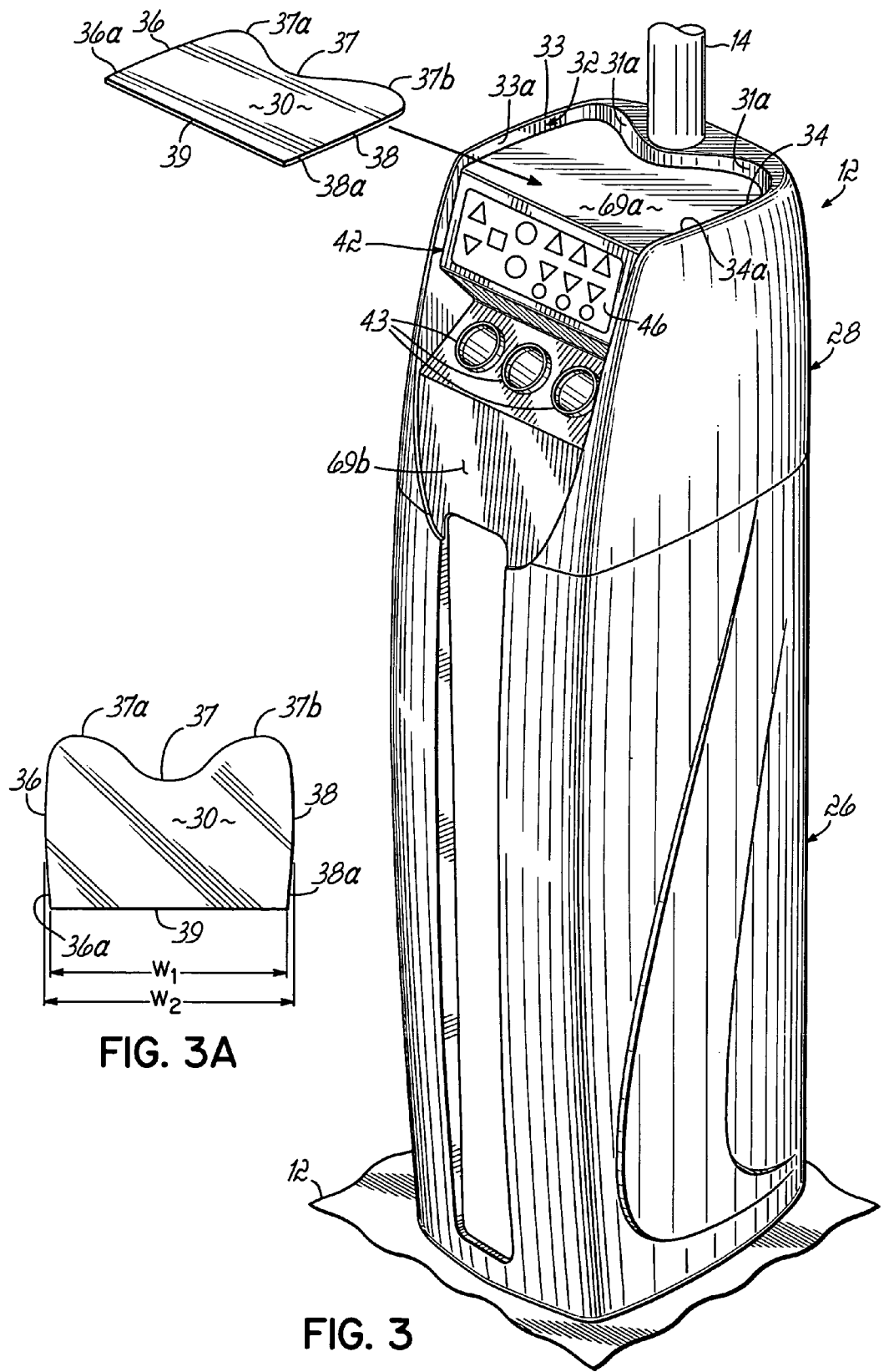
FIG. 3 is a view of the console housing of the instrument stand of FIG. 1.
FIG. 3A is a top view of the removable shelf shown removed from the instrument stand for clarity.

With reference to FIGS. 3 and 3A, the ophthalmological instrument stand 10 includes a shelf 30, which may be formed from any polymer resin material including, but not limited to, an acrylic-based polymer or a polycarbonate like LEXAN® available from GE Plastics, that is removably installed on top of the console housing 28. The shelf 30 is positioned above a relatively thin case portion 69a of an electronics module 42 and is in contact with case portion 69a. The case portion 69a is supported on a support surface 29 (FIG. 4) defined as a ledge or ridge projecting into a module-receiving space 40 and extending about the interior of the console housing 28. The support surface 29 and case portion 69a collectively support shelf 30.

The support surface 29 of the console housing 28 is recessed below the top of the console housing 28 and, when covered by case portion 69a, defines a horizontal plane 35. The support surface 29 is surrounded by a contoured wall 32 defined as a portion of console housing 28 and is also in horizontal plane 35. The support surface 29 and contoured wall 32 have similar contours. Contoured wall 32 includes opposed side walls 33, 34 with respective side wall portions 33a, 34a that are separated by a distance $W_3$ representing a line in the horizontal plane 35 extending between the side wall portions 33a, 34a at the elevation of the shelf 30. The side wall portions 33a, 34a have a greater separation or width in horizontal plane 35 rearward of this line.

The shelf 30 has a contoured periphery or perimeter including a rear edge 37, a front edge 39, and side edges 36, 38 extending between the rear and front edges 37, 39 and each intersecting the front edge 39 at a respective non-perpendicular angle. The rear edge 37 of shelf 30 includes curved edge portions 37a and 37b that converge at a smoothly curved central junction. The curved edge portions 37a,b are contoured with curvatures that match respective curvatures of corresponding curved rear wall portions 31a,b defined in contoured wall 32. Similarly, the side edges 36, 38 of the shelf 30 are contoured to match the side walls 33, 34.

Shelf 30 is installed from a position above the console housing 28 by vertically lowering the shelf 30 into the console housing 28 to a position above support surface 29 and in contact with case portion 69a. Similarly, the shelf 30 may be vertically raised from the console housing 28 for removal to, for example, clean soiled surfaces or for replacement. The complementary contouring of the side walls 33, 34 and side edges 36, 38, respectively, provide a self-aligning function when placing the shelf 30 on the console housing 28. When the shelf 30 is installed, the side walls 33, 34 and side edges 36, 38 will naturally line up to form an accurate mating relationship. This facilitates assembly without precise alignment.

When the shelf 30 is installed above the support surface 29, the front edge 39 is collinear with the line in horizontal plane 35 at which the side wall portions 33a, 34a are separated by width $W_3$. The distance between side edge portions 36a, 38a narrows near the front edge 39 of shelf 30. Specifically, the shelf 30 has a first width, $W_1$, measured between side edge portions 36a, 38a at the front edge 39, that is slightly less than the distance $W_3$ separating the side wall portions 33a, 34a at the front edge of the horizontal plane 35, which provides a clearance so that the side edge portions 36a, 38a will fit between the side wall portions 33a, 34a. The shelf 30 also has a second width, $W_2$, measured between side edge portions 36a, 38a rearward of the front edge 39 that is greater than the width of the distance $W_3$ between the side wall portions 33a, 34a and, accordingly, that is also greater than the first width, $W_1$.

Preferably, the side edge portions 36a, 38a are curved inwardly toward the front edge 39 and the side wall portions 33a, 34a are curved inwardly with a similar curvature. Side wall portion 33a and side edge portion 36a have substantially the same curvature. Similarly, side wall portion 34a and side edge portion 38a have substantially the same curvature.

As a result of the progressive widening of the shelf 30 in a direction away from the front edge 39 relative to the width $W_3$, the installed shelf 30 resists removal from the support surface 29 of console housing 28 when a horizontal force is applied to the shelf 30 in a forward direction away from the support pole 14. However, the shelf 30 may be easily removed by lifting the shelf 30 vertically from the support surface 29 so that the inwardly curved side edge portions 36a, 38a are disengaged from the side wall portions 33a, 34a and then applying a horizontal force in a direction away from the support pole 14.

Figure 4:
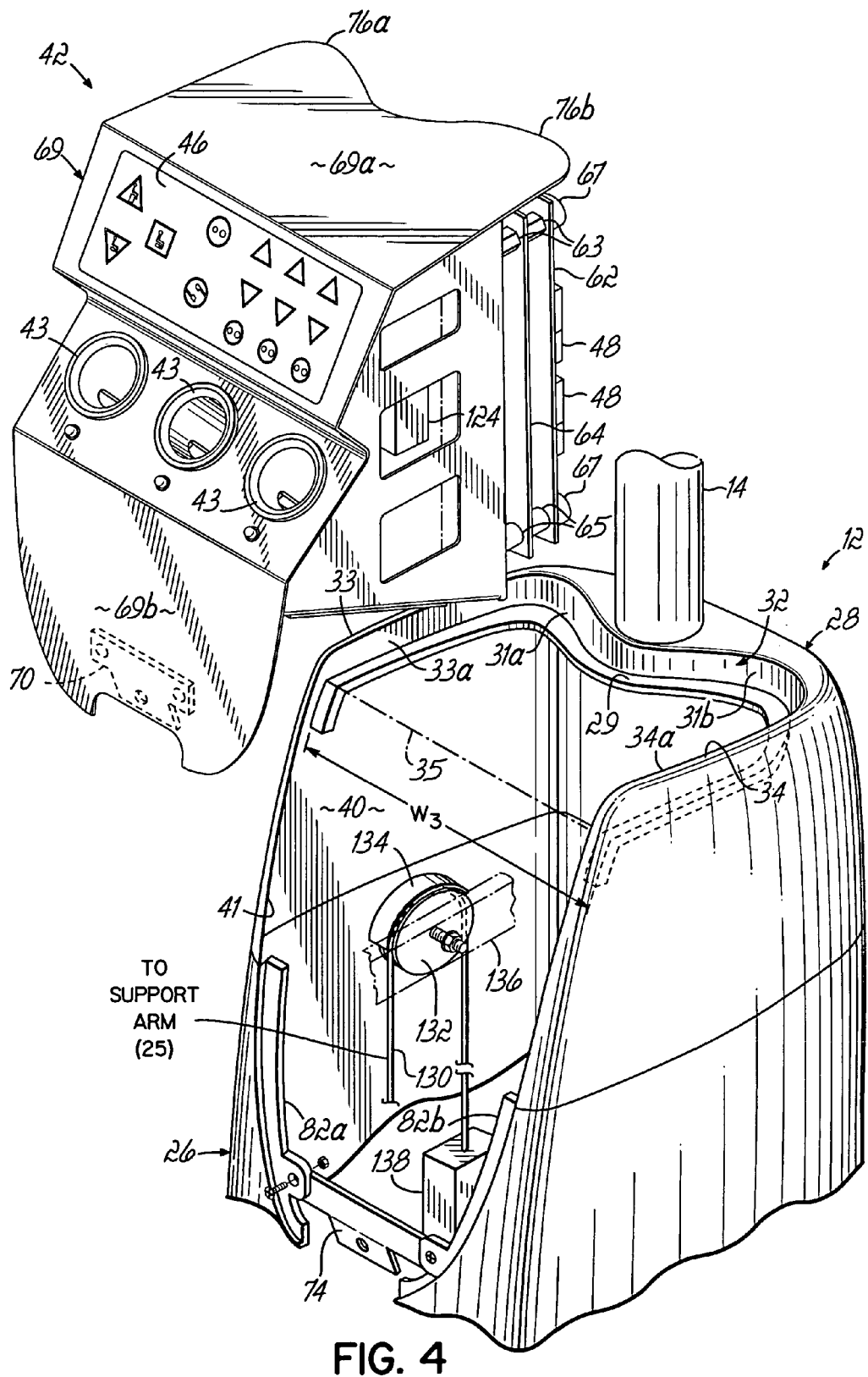
FIG. 4 is an exploded view of a portion of the console housing of FIG. 3 showing the removability of an electronics module.
Figure 5:
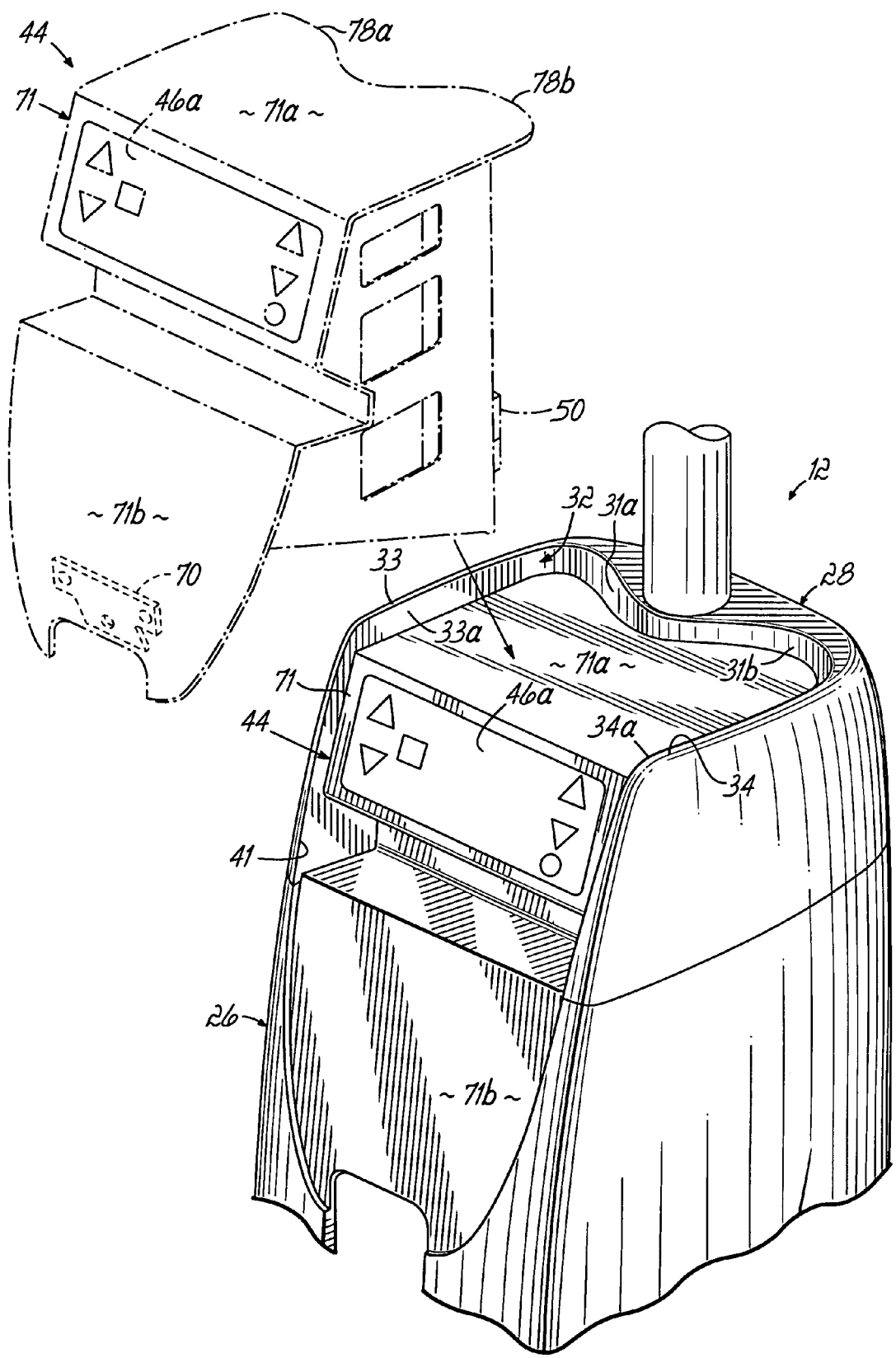
FIG. 5 is a view similar to FIG. 4 showing a different electronics module installed in the console housing.

With reference to FIGS. 3-5, a module-receiving space, generally indicated by reference numeral 40 (FIG. 4), is provided inside the base 12 of the ophthalmological instrument stand 10. Module-receiving space 40 is configured to removably accept any of a plurality of different electronics modules, including but not limited to an electronics module 42 (FIG. 4) and an electronics module 44 (FIG. 5). The module-receiving space 40 is defined partially inside the console housing 28 and partially inside the lower housing 26. An entrance to the module-receiving space 40 is surrounded by a rim 41. The installation of electronics module 44 in the console housing 28 is illustrated in FIG. 5.

Each of the electronics modules 42, 44 may be removed from the front of the base 12 for exchange by disconnecting corded plugs from electrical connectors, such as electrical connectors 48 on the backside of electronics module 42 or electrical connectors 50 on the backside of electronics module 44, and removing conventional fasteners securing the mounted one of the electronics modules 42, 44 to the console housing 28. The procedure is reversed to install one of the electronics modules 42, 44 in the module-receiving space 40. The hidden backside of the installed one of the electronics modules 42, 44 and the module-receiving space 40 are accessed by removing a removable back cover 49 of the base 12.

The ability to easily insert and remove the electronics modules 42, 44 from the front of ophthalmological instrument stand 10 provides ease and convenience in interchanging the electronics modules 42, 44. For example, electronics module 42 includes recharging wells 43 each of which may hold a corresponding ophthalmic instrument (not shown) for recharging, and a control pad 46 populated by controls for controlling the operation of, for example, the medical instruments 20a, 20b supported by support arms 20, 22, the chair in which the patient is seated, lamp 16, the room lights, and other devices associated with ophthalmological instrument stand 10 and ophthalmological procedures. One such device is a projector for an eye chart on a screen or wall during a procedure. Electronics module 44 includes a control pad 46a but lacks recharging wells equivalent to recharging wells 43 of electronics module 42 and several individual controls found on control pad 46 of module 42.

The electronics modules 42, 44 each house electrical circuits and other electrical components (not shown) necessary for the operation of the medical instruments 20a, 20b of the ophthalmological instrument stand 10. One or both of the electronics modules 42, 44 may also optionally include additional electrical circuits and electrical components (not shown) for operating other devices in the examination room, such as a lamp circuit for regulating the room lighting level. Generally, the controls on the control pads 46, 46a are used to control electrical circuits and components housed inside the respective electronics modules 42, 44. Various circuit configurations may be designed into the circuits inside the electronics modules 42, 44. The circuit configurations will vary widely depending upon the particular requirements of each individual application. For example, electronics module 42 will include an electrical circuit for operating the recharging wells 43 that is absent from, or disabled in, electronics module 44.

The interchangeability and modularity of the electronics modules 42, 44 also eases repair or replacement of a faulty or malfunctioning module 42, 44. For example, under these circumstances, a faulty electronics module 42 may be easily replaced with another electronics module 42 having identical electrical circuits and components. This permits repairs to be made while the electronics module 42 is removed from the base 12 or, alternatively, speeds any repair process as the faulty module 42 may be quickly replaced. The ease of repair or replacement applies equally to electronics module 44.

Electronics module 42, which is shown installed in the module-receiving space 40, includes a case 69 of a conductive material, such as a metal, that houses its electrical circuits and components. Similarly, electronics module 44 includes a case 71 of a conductive material, such as a metal, that houses its electrical circuits and components. The cases 69, 71 are dimensioned to fit within the confines of the module-receiving space 40. Case 69 includes case portion 69a having a periphery shaped to conform to the shape of the contoured wall 32 above shoulder 29 and the vertical entrance to module-receiving space 40. Similarly, a case portion 71a of case 71 has a similarly shaped periphery. Case 69 also includes a case portion 69b having a periphery shaped to conform to the nearby portions of rim 41 surrounding the horizontal entrance to module-receiving space 40. Similarly, a case portion 71b of case 71 of electronics module 44 has a similarly shaped periphery.

Electronics module 42 is provided with components that supply additional circuitry for providing additional functionality as compared with electronics module 44. To that end, electronics module 42 includes a chassis plate 62 that is grounded relative to the stand power supplies (not shown) and a circuit board 64 carrying the additional circuitry. At three corners, the chassis plate 62 and circuit board 64 are separated from the case 69 of the electronics module 42 by insulating mounting posts 63, which are threaded together through a corresponding clearance opening in the circuit board 64. The mounting post 63 positioned between the circuit board 64 and the case 69 has a threaded engagement with the case 69. A conventional fastener (not shown) is used to couple the chassis plate 62 with the mounting post 63 positioned between the chassis plate 62 and circuit board 64.

At the fourth corner, the chassis plate 62 and circuit board 64 are separated from the case of the electronics module 42 by insulating washers 65 having a central opening. The bore of each annular insulating washer 65 is aligned with registered clearance openings in the chassis plate 62 and circuit board 64. A bolt 67, which is inserted through the registered bores and openings, has a threaded tip that is fastened to the case of the electronics module 42 and is formed of a conductive material that provides a ground path from the electronics module 42 to the grounded chassis plate 62. The insulating mounting posts 63 and the insulating washers 65 are formed from a material of relatively-high electrical resistivity, such as nylon. The chassis plate 62 and circuit board 64 are omitted from electronics module 44.

With continued reference to FIGS. 3-5, each of the electronics modules 42, 44 includes a respective tab 70 configured to be attached with a conventional fastener to a support bar 74 mounted to the lower housing 26 and positioned near the horizontal entrance to the module-receiving space 40 along the front side of the base 12. The case portion 69a of the electronics module 42 includes curved edges 76a,b that align with the rear wall portions 31a,b of the console housing 28 above the support surface 29. Similarly, a case portion 69a of the case 69 includes identical curved edges 78a,b for alignment.

Support surface 29 of the console housing 28 and support surfaces 82a, 82b defined in the lower housing 26 cooperate to aid in securing the installed one of the electronics modules 42, 44 in the module-receiving space 40 of console housing 28. Support bar 74 is secured by conventional fasteners with a tab 70 mounted to each of the electronics modules 42, 44. Opposite sides of the support bar 74 are mounted with conventional fasteners to corresponding threaded openings defined in ears projecting from each of the support surfaces 82a, 82b. When electronics module 42, for example, is installed in the module-receiving space 40, the curved edges 76a,b abut the rear wall portions 31a,b, a fastener secures the support bar 74 with tab 70, the periphery of case portion 69b contacts the support surfaces 82a, 82b, suitable electrical plugs (not shown) are engaged with electrical connectors 48 on the backside of the electronics module 42, and the periphery of case portion 69a contacts support surface 29 with curved edges 78a,b aligned with rear wall portions 31a,b. The back cover 49 is removed to access the module-receiving space 40, with electronics module 42 in position, for mating the electrical connectors 48 and plugs and to fasten the tab 70 with support bar 74. Case portion 69a is recessed below the vertical entrance to the module-receiving space 40 and, hence, rim 41 and case portion 69b is recessed below or flush with rim 41 at the horizontal entrance to module-receiving space 40.

With reference to FIGS. 6A and 6B, located on a first side surface 45a of section 25b of the support arm 25 is an opening or cutout 47 shaped, for example, to accept respective electrical inserts 52, 54, 56, such as a socket, a toggle switch, or a push button. Section 25c is omitted from FIGS. 6A, 6B for purposes of clarity in illustration. Cutout 47 is substantially trapezoidal, although the invention is not so limited, as the shape of the cutout 47 corresponds to the shape of a panel 55.

The electrical inserts 52, 54, 56 may be carried in corresponding openings 90, 92, 94 defined on panel 55 that is secured by conventional fasteners to the arm section 25b. Alternatively, the electrical inserts 52, 54, 56 may be directly attached to the arm section 25b, and panel 55 may function as a cover panel that does not directly support the inserts 52, 54, 56. Under these circumstances, openings 90, 92, 94 would serve as clearance openings. In another alternative embodiment of the present invention, openings 90, 92, 94 in panel 55 may support some inserts 52, 54, 56 and not others. Unused openings 90, 92, 94 may be plugged or covered for those applications not requiring all inserts 52, 54, 56.

Cutout 47 is dimensioned to have proper clearance to receive electrical inserts 52, 54, 56 and defines an access path to a hollow interior space 86 of section 25b, which is tubular. Electrical wires associated with the inserts 52, 54, 56, of which only wires 99 for insert 56 are shown in FIG. 6A, are routed through a service conduit defined by the hollow interior space 86 of section 25b and the hollow interior space of section 25a, which is also tubular, into the module-receiving space 40 and to the installed one of the electronics modules 42, 44. When installed, panel 55 is substantially flush or coplanar with side surface 45a of the arm section 25b as the panel 55 fits within a recess 57 defined in section 25b.

One or more cutouts 60 on an opposite second side surface 45b of section 25b are covered by a blank cover panel 58 that blocks access to the interior space 86 inside section 25b. When installed, cover panel 58 is substantially flush or coplanar with side surface 45b of arm section 25b as the cover panel 58 fits within a recess 61 defined in section 25b. Panels 55, 58 and recesses 57, 61 are generally trapezoidal in shape with a pair of curved corners, although the invention is not so limited. The geometrical shapes are matched such that the width of any gaps between the panels 55, 58 and the corresponding recesses 57, 61 are minimized.

As shown in FIG. 6C, a panel 95 is configured to be coupled with the recess 61 and includes openings 96, 98, 100 for electrical inserts 52, 54, 56, respectively. Panel 95 has a construction similar to that of panel 55 (FIG. 6A). When panel 95 is mounted to the second side surface 45b of section 25b, the blank cover panel 58 is moved to cover recess 57 in side surface 45a and block access to interior space 86.

The invention contemplates that openings 90, 92, 94 and openings 96, 98, 100 may be arranged in any suitable manner to conveniently locate different types of electrical inserts, such as inserts 52, 54, 56. For example, openings 90, 92, 94 and openings 96, 98, 100 may be ordered such that, for example, openings 90 and 96 are always nearest to section 25c. This arrangement, as shown in FIGS. 6A-C, would necessitate the use of another panel 95 in addition to panel 55 to provide the ability to change the support arm 25 from a configuration for use by a right-handed user to a configuration for use by a left-handed user. Alternatively, the openings 96, 98, 100 may be arranged such that panel 55 is positionable in either recess 57 on side surface 45a or in recess 61 on side surface 45b.

One of the panels 55, 95 is positioned in cutout 47 (FIG. 6A) on side surface 45a or cutout 60 on side surface 45b, which permits the location of electrical inserts 52, 54, 56 to be selected from between side surface 45a and 45b during manufacture or at the installation location. The blank cover panel 58 is used to cover the unused cutout, such as unused cutout 60 when panel 55 is mounted in cutout 47. In this manner, the support arm 25 may be reconfigured without replacing the entire assembly. Specifically, the ability to swap the location of the electrical inserts 52, 54, 56 permits the ophthalmological instrument stand 10 to be easily adapted for use by either left-handed or right-handed users. To that end, section 25b of support arm 25 may have a rectangular cross-section profile and the first and second side surfaces 45a, 45b may be substantially vertical and parallel surfaces defining opposite sides of the rectangular cross-sectional profile.

Figure 7:
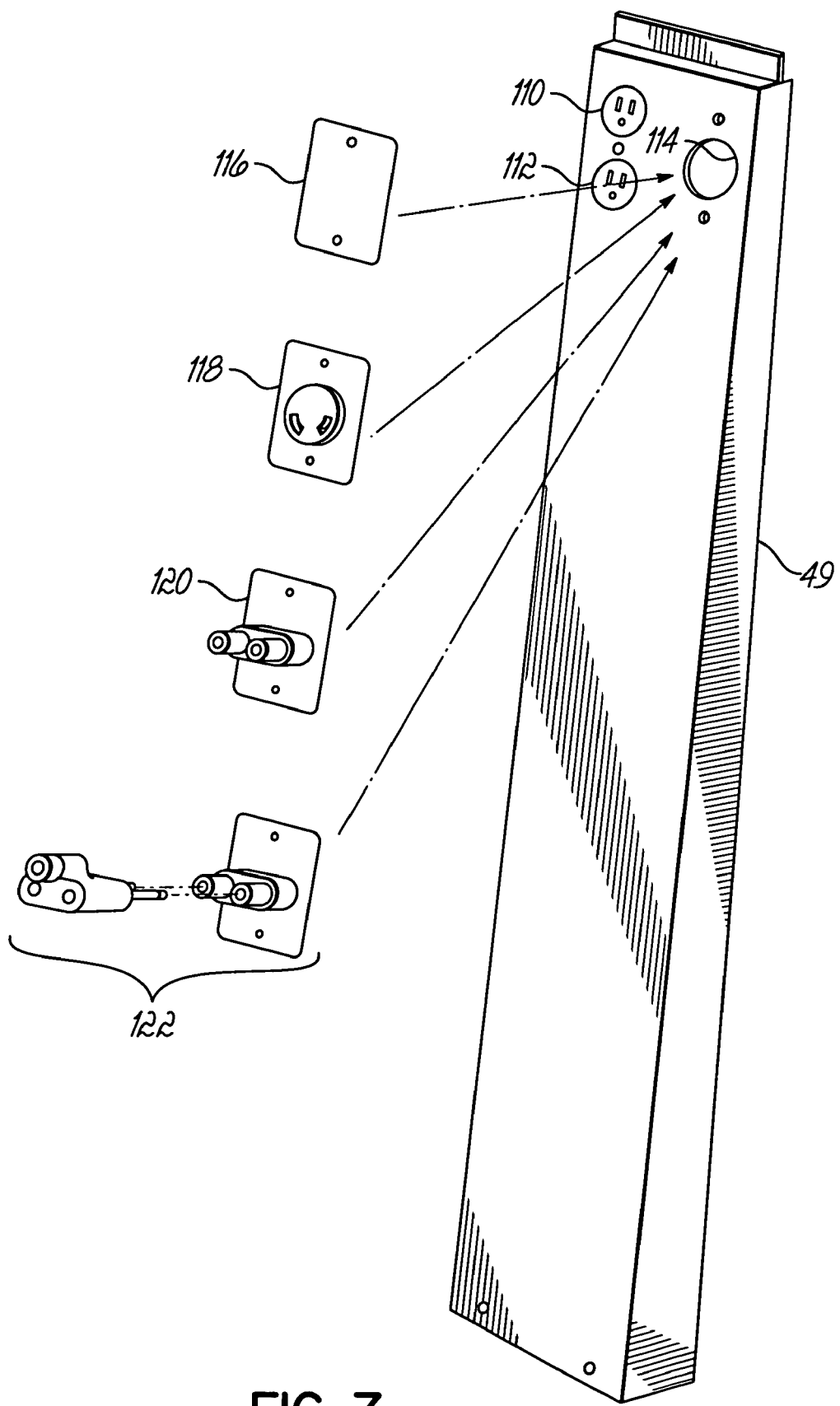
FIG. 7 is a rear perspective view of the back cover of the instrument stand of FIG. 1, in which the back cover has been removed from the instrument stand for clarity.

With reference to FIG. 7, the back cover 49 includes a pair of electrical receptacles 110, 112 that receive corded plugs (not shown) for powering other devices in the examination room. For example, power cords for medical instrument 20b and another device, such as an eye chart projector, may each be corded to plug into a corresponding one of the receptacles 110, 112. An opening 114, which may be circular, is also defined in the back cover 49. The opening 114, if unused, is covered by a blank panel 116. Alternatively, the opening 114 may be filled by one of a plurality of receptacles, including but not limited to a Hubbell twist-lock receptacle 118, a banana plug receptacle 120 that may optionally accept bare wires, or a banana plug receptacle provided with a phono jack adapter to create a phono jack receptacle 122. The installed one of the receptacles 118, 120, 122 is coupled with a power supply 124 inside electronics module 42. In one embodiment of the present invention, the installed one of the receptacles 118, 120, 122 powers a portable lamp, which may be mounted by a band to the physician's head, having a corded plug inserted into the installed one of the receptacles 118, 120, 122.

The ability to selectively install either receptacle 118, receptacle 120 in one of its versions, or receptacle 122 in opening 114 permits different types of power cords to be powered, which enhances compatibility. The ability to remove back cover 49 provides convenient access to the opening 114 for installing one of the receptacles 118, 120, 122. This is a benefit of this aspect of the present invention as compared with conventional hard-wired receptacles that are located, for example, on the console housing 28. After the back cover 49 is removed, the installed one of the receptacles 118, 120, 122 is removed and a different one of the receptacles 118, 120, 122 is installed.

With renewed reference to FIG. 4, the instrument stand 10 is provided with a cable 130 that couples a counterweight 138 with support arm 25 for dampening vertical movement of support arm 25 after a locking mechanism 19 (FIG. 2) is released. The cable 130 is engaged with a pulley 132 mounted to a frame member 136 inside the lower housing 26. Extending across an upper surface of the pulley 132 is a curved restraining member or cover 134 that covers at least the portion of pulley 132 that is in contact with the cable 130. The cover 134 projects inwardly from the console housing 28 into the module-receiving space 40 and overlies a groove extending about the circumference of the pulley 132 in which the cable 130 resides. Circumferential flanges defining the groove in the pulley 132 constrain the cable 130 against lateral movement.

The cover 134 is positioned relative to the pulley 132 such that the cable 130 cannot pass between the curved gap separating the pulley 132 from the cover 134. Accordingly, the cover 134 operates to prevent the cable 130 from becoming disengaged from the pulley 132, for example, during shipment or when the instrument stand 10 is installed. In other words, the cover 134 prevents the cable 130 from being derailed off the pulley 132 when, for example, the support arm 25 or counterweight 138 moves vertically relative to base 12 during shipment or if support arm 25 is telescoping rapidly relative to base 12. When the instrument stand 10 is in use, the mass of the counterweight 138 applies a force that urges the cable 130 into contact with the groove of the pulley 132. Friction between the cable 130 and pulley 132 causes the pulley 132 to rotate as the counterweight 138 moves and as the support arm 25 telescopes relative to base 12.

While the present invention has been illustrated by a description of various preferred embodiments and while these embodiments have been described in considerable detail in order to describe the best mode of practicing the invention, it is not the intention of the applicants to restrict or in any way limit the scope of the appended claims to such detail. Additional advantages and modifications within the spirit and scope of the invention will readily appear to those skilled in the art. The invention itself should only be defined by the appended claims, wherein we claim:

We claim:

1. An instrument stand for use with a medical instrument, the instrument stand comprising:

a console housing having a support surface defining a horizontal plane and a side wall surrounding said support surface;

an instrument pole projecting from said base;

a support arm extending from said instrument pole, said support arm configured to support the medical instrument; and a shelf removably supported above said support surface, said shelf having first and second side edges and a front edge connecting said first and second side edges, said first and second side edges being shaped to match said side wall so that said shelf cannot be removed from said console housing by a force applied to said shelf in said horizontal plane, wherein said side wall has opposite first and second side wall portions each adjacent to a corresponding one of said first and second side edges of said shelf, said side wall portions being separated by a first separation distance defined in the horizontal plane at a location coinciding with said front edge of said shelf, and said first and second side edges of said shelf being separated by a second separation distance greater than said first separation distance adjacent to said front edge.

2. The instrument stand of claim 1 wherein said shelf is formed of a material selected from the group consisting of acrylic-based polymers and polycarbonates.

3. An instrument stand for use with a medical instrument, the instrument stand comprising:

a console housing having a support surface defining a horizontal plane and a side wall surrounding said support surface;

an instrument pole projecting from said base;

a support arm extending from said instrument pole, said support arm configured to support the medical instrument; and a shelf removably supported above said support surface, said shelf having first and second side edges and a front edge connecting said first and second side edges, said first and second side edges being shaped to match said side wall so that said shelf cannot be removed from said console housing by a force applied to said shelf in said horizontal plane, wherein said first and second side edges of said shelf are separated by a distance that narrows in a direction toward said front edge, and said side wall has first and second side edge portions with a complementary narrowing such that each contacts a corresponding one of said first and second side wall portions.

4. An instrument stand comprising:

a base;

a support arm extending from said base, said support arm including an interior space and first and second surfaces each including at least one cutout providing access to said interior space;

a first panel removably mounted to said first surface, said first panel configured for covering said at least one cutout in said first surface to block access to said interior space when mounted to said first surface; and a second panel removably mounted to said second surface, said second panel including at least one electrical insert positioned in said at least one cutout in said second surface and said second panel configure for covering said at least one cutout when said second panel is mounted to said second surface.

5. The instrument stand of claim 4 wherein said first panel is further configured to be mounted to said second surface for covering said at least one cutout in said second surface.

6. The instrument stand of claim 4 wherein said base includes an electronics module electrically coupled with said at least one electrical insert.

7. The instrument stand of claim 4 further comprising:

a third panel configured to be removably mounted to said first surface, said third panel including at least one electrical insert positioned in said at least one cutout in said first surface when said third panel is mounted to said first surface.

8. The instrument stand of claim 4 wherein said first panel is further configured to be removably mounted to said second surface, said first panel covering said at least one cutout in said second surface to block access to said interior space when mounted to said second surface.

9. The instrument stand of claim 4 wherein said first and second surfaces are arranged on said support arm to permit said support arm to be optionally configured to allow said at least one electrical insert to be operated by either right-handed users or left-handed users.

10. The instrument stand of claim 4 wherein said second panel includes an opening, and said at least one electrical insert is mounted in said opening.

11. An instrument stand comprising:

a base;

a support arm extending from said base, said support arm adapted to telescope relative to said base;

a counterweight positioned inside said base, said counterweight being adapted to move responsive to telescoping movement of said support arm relative to said base;

a cable coupling said support arm with said counterweight;

a pulley mounted inside said base and having a portion in contact with said cable, said cable causing rotation of said pulley when said counterweight moves; and a curved restraining member extending across at least said portion of said pulley in contact with said cable, said restraining member preventing said portion of said cable from losing contact with said pulley.

12. The instrument stand of claim 11 wherein said curved restraining member projects across a circumferential groove defined in said pulley for receiving said cable.

13. A method of configuring an ophthalmological instrument stand, the method comprising:

removing a first electronics module from a module-receiving space defined in a console housing of the instrument stand, the first electronics module configured with circuitry to control a device associated with the ophthalmological stand; and installing a second electronics module in the module-receiving space, the second electronics module configured with circuitry to control a different device associated with the ophthalmological stand.

14. The method of claim 13 wherein the first electronics module has malfunctioning circuitry, and installing the second electronics module further comprises:

exchanging the first electronics module with malfunctioning circuitry for another first electronics module having operational circuitry.

15. The method of claim 13 wherein the device is an ophthalmological instrument.

16. The instrument stand of claim 3 further comprising:

an instrument pole projecting from said base; and a support arm extending from said instrument pole, said support arm configured to support a medical instrument.

17. The instrument stand of claim 3 wherein said shelf is formed of a material selected from the group consisting of acrylic-based polymers and polycarbonates.

* * * * *

UNITED STATES PATENT AND TRADEMARK OFFICE
CERTIFICATE OF CORRECTION

PATENT NO. : 7,467,871 B2
APPLICATION NO. : 10/978550
DATED : December 23, 2008
INVENTOR(S) : Steven Lee Lawhorn et al.

It is certified that error appears in the above-identified patent and that said Letters Patent is hereby corrected as shown below:

In column 3, line 45, change "0.10" to --10--.

In column 5, line 11, change "38anarrows" to --38a narrows--.

In column 5, line 21, change "34aand" to --34a and--.

In column 11, line 16, change "configure" to --configured--.

Signed and Sealed this

Sixth Day of October, 2009

David J. Kappos
*Director of the United States Patent and Trademark Office*